United States Patent [19]

Seng et al.

[11] 4,263,435
[45] Apr. 21, 1981

[54] 6-[2-HYDROXY-4-(1,2,3-TRIAZOL-2-YL)-PHENYL]-2,4-DIOXO-1,3,5-TRIMETHYL-HEXAHYDRO-S-TRIAZINES AND THEIR PREPARATION

[75] Inventors: Florin Seng, Bergisch Gladbach; Alfons Dorlars, Leverkusen; Carl-Wolfgang Schellhammer, Bergisch Gladbach, all of Fed. Rep. of Germany

[73] Assignee: Bayer Aktiengesellschaft, Leverkusen, Fed. Rep. of Germany

[21] Appl. No.: 87,194

[22] Filed: Oct. 22, 1979

[30] Foreign Application Priority Data

Nov. 9, 1978 [DE] Fed. Rep. of Germany ....... 2848670

[51] Int. Cl.³ .................. C07D 251/10; C07D 249/06
[52] U.S. Cl. ..................................................... 544/223
[58] Field of Search ..................................... 544/223

[56] References Cited
U.S. PATENT DOCUMENTS

| | | | |
|---|---|---|---|
| 3,933,815 | 1/1976 | Ploeg | 544/223 |
| 4,080,502 | 3/1978 | Seng et al. | 544/223 |

*Primary Examiner*—John M. Ford
*Attorney, Agent, or Firm*—Sprung, Felfe, Horn, Lynch & Kramer

[57] ABSTRACT

Triazolylphenyl-triazines of the formula

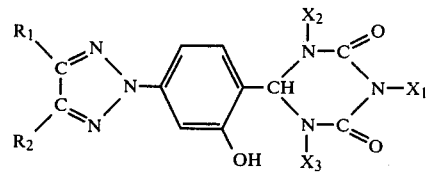

wherein
$R_1$ and $R_2$ denote alkyl or aryl and
$X_1$, $X_2$ and $X_3$ denote alkyl, aralkyl or cycloalkyl, which are obtainable by reacting corresponding 3-hydroxyphenyl-triazoles with corresponding 2,4-dihydroxy-triazinium compounds, are outstandingly suitable for the preparation of 4-(1,2,3-triazol-2-yl)-salicylaldehydes, which in turn are starting materials for the preparation of optical brighteners of the type of the triazolylcoumarins.

4 Claims, No Drawings

6-[2-HYDROXY-4-(1,2,3-TRIAZOL-2-YL)-PHENYL]-2,4-DIOXO-1,3,5-TRIMETHYL-HEXAHYDRO-S-TRIAZINES AND THEIR PREPARATION

The present invention relates to triazolylphenyltriazines of the formula

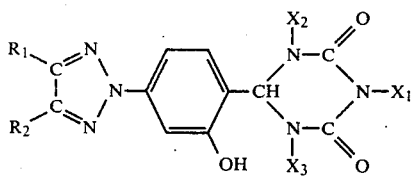

wherein $R_1$ and $R_2$ denote optionally substituted alkyl or aryl and $X_1$, $X_2$ and $X_3$ denote optionally substituted alkyl, aralkyl or cycloalkyl.

Suitable alkyl radicals are those with 1 to 4 C atoms, which preferably are not substituted further and have a straight chain.

Suitable aryl radicals are phenyl radicals which can be mono-, di- or tri-substituted by halogen, $C_1$-$C_4$-alkyl or $C_1$-$C_4$-alkoxy; examples which may be mentioned are phenyl, tolyl, xylyl, chlorophenyl, dichlorophenyl or methoxyphenyl.

Preferably, $R_1$ and $R_2$ represent methyl, ethyl or phenyl and $X_1$, $X_2$ and $X_3$ represent methyl.

"Halogen" within the scope of the present invention above all means F, Br and especially Cl.

According to the invention, the compounds of the formula I are prepared by reacting 3-[1,2,3-triazol-2-yl]-phenols of the formula II

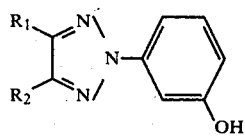

wherein $R_1$ and $R_2$ have the abovementioned meaning, with compounds of the formula

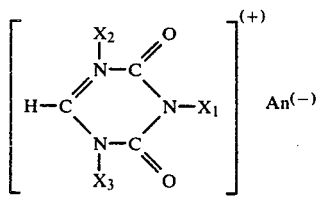

wherein $X_1$, $X_2$ and $X_3$ have the abovementioned meaning and $An^{(-)}$ represents an anion, preferably $Cl^{(-)}$ or $Br^{(-)}$, in the presence of an acid acceptor.

The phenols of the formula II are known (compare Liebigs Annalen der Chemie 1978, page 345 et seq.) or are obtainable in a manner which is in itself known, for example by diazotising the corresponding aniline derivatives and boiling the resulting diazonium salts.

The triazinium salts of the formula III are also known (compare Synthesis 1977, page 753) and are disclosed in detail in, for example, British Pat. Specification No. 1,477,937, page 2, lines 43–55.

Suitable acid acceptors are above all organic bases, especially tertiary amines, such as, for example, triethylamine, tri-n-propylamine, tri-n-butylamine and dimethylbenzylamine.

These bases are employed in at least molar amounts (relative to (III)).

The reaction of (II) with (III) is advantageously carried out in a polar organic solvent at temperatures of 80°–140° C., preferably 90°–110° C., and in this reaction the molar ratios of II/III should be from 1:1 to 1:1.5.

Suitable solvents are dimethylformamide, tetramethylurea, dimethylsulphoxide and others. The reaction times are 1–30 hours.

The compounds according to the invention, of the formula (I), are valuable intermediates for the preparation of 4-(1,2,3-triazol-2-yl)-salicylaldehydes, which in turn are starting materials for the preparation of optical brighteners of the type of the triazolylcoumarins (compare U.S. Pat. Nos. 4,005,098, 3,496,188, 3,646,052 and British Pat. Specification No. 1,313,253).

Compared to the known processes for the preparation of these coumarin compounds, which start from 4-(N-acylamino)-salicylaldehydes, the new process, using the compounds of the formula (I) as starting materials, is distinguished by a smaller number of reaction steps and hence by an improved space/time yield.

The cleavage of the compounds of the formula (I) to give the corresponding free aldehydes takes place in a manner which is in itself known, by alkaline hydrolysis (compare British Pat. Specification No. 1,477,937) and subsequent working up under acid conditions.

In practice, the hydrolysis is carried out at temperatures of 90°–150° C. in water or a water-miscible organic solvent (for example n-butanol or methylglycol) in the presence of 5–20 mols of alkali (for example NaOH or KOH) per mol of the compound (I).

This hydrolysis initially gives the alkali metal salts of the aldehydes, which are converted to the free salicylaldehydes by means of mineral acids, such as hydrochloric acid or sulphuric acid.

The reaction of these aldehydes with arylacetic acids or hetarylacetic acids in acetic anhydride in the presence of sodium acetate, by a Perkin reaction, finally gives the corresponding coumarin brighteners.

Suitable arylacetic acids and hetarylacetic acids for carrying out this reaction are phenylacetic acid and its halogen-, $C_1$-$C_4$-alkyl- and/or $C_1$-$C_4$-alkoxy-derivatives, pyrazolylacetic acid, 1,2,3-triazol-1-yl-acetic acid, 1,2,4-triazolylacetic acid and their halogen- and $C_1$-$C_4$-alkyl-derivatives.

EXAMPLE 1

6-[2-Hydroxy-4-(4-methyl-5-phenyl-1,2,3-triazol-2-yl)-phenyl]-2,4-dioxo-1,3,5-trimethyl-hexahydro-s-triazine A mixture of 268 g (1.4 mols) of 2,4-dioxo-1,3,5-trimethyl-tetrahydro-s-triazinium chloride, 251 g (1 mol) of 2-[3-hydroxyphenyl]-4-phenyl-5-methyl-v-triazole and 189 g (1.4 mols) of dimethylbenzylamine in 400 ml of dimethylformamide is stirred for 11 hours at 100° C. 380 ml of dimethylformamide are then evaporated off in a waterpump vacuum at a bath temperature of 90° C. and 500 ml of water are added to the residue. Hereupon, 390 g of crude material, of 82.9% purity, separate out, corresponding to a yield of 79.5%. Melting point, after recrystallisation from acetic acid: 252° C.

Analysis $C_{21}H_{22}N_6O_3$ (406); calculated: C 62.0%; H 5.3%; N 20.7%; found: 62.3%; 5.1%; 20.7%.

If instead of 2-[3-hydroxyphenyl]-4-phenyl-5-methyl-v-triazole, 2-[3-hydroxyphenyl]-4-ethyl-5-methyl-v-triazole is used in the above reaction, the corresponding 6-[2-hydroxy-4-(4-methyl-5-ethyl-1,2,3-triazol-2-yl)-phenyl]-2,4-dioxo-1,3,5-trimethyl-hexahydro-s-triazine, of melting point 196° (after recrystallisation from methanol), is obtained.

EXAMPLE 2

4-[4-Methyl-5-phenyl-1,2,3-triazol-2-yl]-salicylaldehyde

A mixture of 570 g of 6-[2-hydroxy-4-(4-methyl-5-phenyl-1,2,3-triazol-2-yl)-phenyl]-2,4-dioxo-1,3,5-trimethyl-hexahydro-s-triazine, 2,940 ml of water and 560 g of sodium hydroxide is heated for 22 hours at 102° C. It is then cooled to 15° C. and the sodium salt which has separated out is filtered off and introduced into a mixture of 700 g of ice, 700 ml of water and 237 ml of 37% strength hydrochloric acid. After stirring for four hours, the salicylaldehyde produced is filtered off, washed with ice water and dried at 80° C. This gives 353 g of product of melting point 121°–123° C., the product being 98.6% pure, according to analysis. The yield is 89% of theory.

The product is sufficiently pure for further conversions to 7-triazolylcoumarins.

EXAMPLE 3

4-[4-Methyl-5-ethyl-1,2,4-triazol-2-yl]-salicylaldehyde 95 g of 6-[2-hydroxy-4-(4-methyl-5-ethyl-1,2,3-triazol-2-yl)-phenyl]-2,4-dioxo-1,3,5-trimethyl-hexahydro-s-triazine are introduced into a solution of 74.2 g of sodium hydroxide in 930 ml of water at 40° C.; the mixture is boiled under reflux for 18 hours, under nitrogen. The contents of the reaction vessel are then poured out onto 1 kg of ice and 170 ml of 37% strength hydrochloric acid and the mixture is stirred for 4 hours. The product which has separated out is filtered off, washed with ice water and dried at 50° C. 59 g (80% of theory) of the abovementioned salicylaldehyde, of melting point 86°–88° C., are isolated. According to analysis, the product is 83.1% pure.

The product is sufficiently pure for further conversions to 7-triazolylcoumarins.

EXAMPLE 4

7-[4-Methyl-5-phenyl-1,2,3-triazol-2-yl]-3-[4-chloropyrazol-1-yl]-courmarin 49.2 g (0.6 mol) of anhydrous sodium acetate, 96.4 g (0.6 mol) of 4-chloropyrazol-1-yl-acetic acid and 139.7 g (0.5 mol) of 4-[4-methyl-5-phenyl-1,2,3-triazol-2-yl]-salicylaldehyde obtained according to Example 2 are introduced successively into 255 g (2.5 mols) of acetic anhydride, whilst stirring. The mixture is heated to the reflux temperature over the course of 18 hours. It is then cooled to 100° C. and 96 g (3 mols) of methanol are added, whilst cooling further. It is then cooled to +10° C. and the product which has separated out is filtered off. After washing the product with glacial acetic acid, methanol and warm water, and drying at 100° C., 157.2 g of crude material are obtained, and are recrystallised from 2 kg of 1,2-dichlorobenzene. The yield of the abovementioned coumarin is 131.2 g.

EXAMPLE 5

7-[4-Methyl-5-phenyl-1,2,3-triazol-2-yl]-3-phenyl-coumarin

If instead of the 4-chloropyrazol-1-yl-acetic acid employed in Example 4, 81.7 g (0.6 mol) of phenylacetic acid are used, 127.1 g of the abovementioned 3-phenyl-coumarin are isolated as the reaction product.

EXAMPLE 6

7-[4-Methyl-5-ethyl-1,2,3-triazol-2-yl]-3-[1,2,4-triazol-1-yl]-coumarin

A mixture of 23.1 g (0.1 mol) of 4-[4-methyl-5-ethyl-1,2,3-triazol-2-yl]-salicylaldehyde, 15.3 g (0.12 mol) of 1,2,4-triazol-1-yl-acetic acid, 9.8 g (0.12 mol) of anhydrous sodium acetate and 51 g (0.5 mol) of acetic anhydride is boiled under reflux for 12 hours. After working up as above, 22.6 g of 7-[4-methyl-5-ethyl-1,2,3-triazol-2-yl]-3-[1,2,4-triazol-1-yl]-coumarin are obtained.

We claim:

1. A triazolylphenyltriazine of the formula

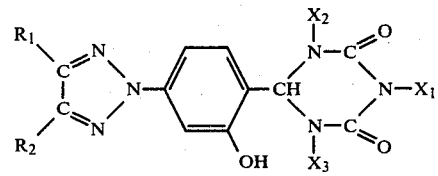

wherein
$R_1$ and $R_2$ each independently is $C_1$–$C_4$-alkyl, phenyl or phenyl substituted by halogen, $C_1$–$C_4$-alkyl or $C_1$–$C_4$-alkoxy,
$X_1$, $X_2$ and $X_3$ each independently is $C_1$–$C_4$-alkyl, cycloalkyl or $C_1$–$C_4$-alkylphenyl optionally substituted on the phenyl by halogen, $C_1$–$C_4$-alkyl or $C_1$–$C_4$-alkoxy.

2. A triazolylphenyltriazine according to claim 1, wherein $R_1$ and $R_2$ each independently is methyl, ethyl or phenyl, and $X_1$, $X_2$ and $X_3$ each methyl.

3. A process for the preparation of a triazolylphenyltriazine according to claim 1, comprising reacting a triazolylphenol of the formula

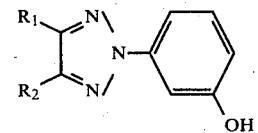

with a compound of the formula

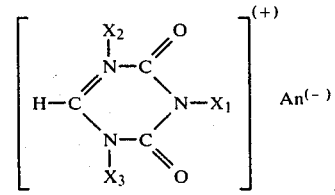

wherein
$An^{(-)}$ is an anion, in the presence of an acid acceptor.

4. A process according to claim 3, wherein the reaction is carried out at 80°–140° C.

* * * * *